United States Patent [19]

Soukup

[11] Patent Number: 5,221,532
[45] Date of Patent: Jun. 22, 1993

[54] *COULTERIA TINCTORIA* POD EXTRACT HAIR TREATMENT COMPOSITION

[76] Inventor: Vaclav Soukup, Rua, No. 140, Apt. 302, Ilha do Governador, Rio de Janeiro - RJ, Brazil

[21] Appl. No.: 837,980

[22] Filed: Feb. 20, 1992

Related U.S. Application Data

[63] Continuation-in-part of Ser. No. 399,915, Aug. 29, 1989, Pat. No. 5,182,110.

[51] Int. Cl.$^5$ ............................ A61K 7/09; A61K 7/11
[52] U.S. Cl. .............................. 424/71; 424/74; 424/195.1; 8/438; 8/528; 8/646
[58] Field of Search ............... 424/195.1, 71, 74; 8/528, 646, 438

[56] References Cited
PUBLICATIONS

Kajima et al, Chemical Abstracts, vol. 107, #20, p. 477, 183331d, 1987.
Kano, Chemical Abstracts, vol. 104, #10, p. 376, 1986 74807f.
Noda et al, Chemical Abstracts, vol. 89, #21, p. 474, 1978, 178363w.
Nogawa et al, Chemical Abstracts, vol. 89, #14, p. 439, 1978, 117555p.

*Primary Examiner*—José G. Dees
*Assistant Examiner*—Deborah D. Carr
*Attorney, Agent, or Firm*—Howard L. Rose

[57] ABSTRACT

A composition for treating hair including Coulteria tinctoria pod extract activated by high temperatures, which composition is formulated into a thixotropic paste or cream for direct application to hair, subjecting the hair to the composition for a selected time, washing, setting and drying the hair.

6 Claims, No Drawings

*COULTERIA TINCTORIA* POD EXTRACT HAIR TREATMENT COMPOSITION

RELATED APPLICATIONS

This Application is a continuation-in-part of U.S. application Ser. No. 07/399,915 filed Aug. 29, 1989, now U.S. Pat. No. 5,182,110.

This invention relates to hair styling involving treatment and particularly to composition and methods employing an extract of the pod of Coulteria tinctoria.

BACKGROUND OF THE INVENTION

Hair treatment (conditioning, reshaping, relaxing and dyeing of human hair) is a substantial part of the cosmetic and beautician industry. Huge sums of money are spent on products and services in salons and in the home.

There exists a vast array of compositions for those purposes, many of them harsh and difficult to use, requiring the skill of hairdressers, in order not to damage the hair.

In the context of conventional materials used for the reshaping of hair, commonly referred to as giving "a permanent," there are two broad classes. The first includes malodorous thio-alcohol/acid derivatives such as thioglycolic acid, thiopropionic acid, monothioglycerol, etc. Treatment includes a rinse step with an appropriate oxidizer in a carefully controlled application.

The second general treatment involves the use of relatively strong caustic alkaline solutions formed from hydroxides of alkali and alkaline earth elements such as sodium hydroxide, calcium hydroxide, etc. With such treatment, it is necessary to further treat the hair with a neutralizing wash to obtain a physiologically compatible pH. It is known in the cosmetic industry that both of the above-specified treatments are harsh and may adversely affect the scalp or, if employed improperly, the hair itself. For example, the "neutralizing" step requires careful application in order to prevent exposure of the hair to too much or too little of the appropriate reagents.

SUMMARY OF THE PRESENT INVENTION

It is an object of this invention to provide a novel composition and method for using a composition for treatment of human hair.

It is another object of this invention to provide a composition for treatment of human hair which is safe and does not damage the hair and/or irritate the scalp during treatment.

Still another object of this invention is to provide a composition and method for treating the hair absent the use of caustic and other harsh reagents.

Yet another object of this invention is to utilize a readily available, inexpensive natural product extract, which is easily employed either by an individual at home or by a professional in a salon.

A further object of this invention is to provide effective hair treatment that conditions, relaxes and reshapes the hair without reducing its tensile strength, increases its softness and luster and dyes it.

These and other objects are satisfied by a composition of matter for treating hair comprising Coulteria tinctoria pod extract, prepared and/or treated preferably at elevated temperatures, compounded with a suitable vehicle, maintaining the composition on the hair for a desired period of time, washing the composition from the hair and drying the hair.

The instant invention utilizes the discovery, that the extract of the Coulteria tinctoria pod, preferably treated during the extraction or afterward at elevated temperatures, temperatures in excess of 100° C., relaxes, conditions, and dyes the hair. The treated hair is softer, shinier, dark coloured, and shows remarkable tendency to retain the desired shape.

The pods are produced by the Coulteria tinctoria tree, native to tropical South America, the tree being a member of the family Leguminosae.

Since the pod extract is derived from a common plant, it is plentiful and inexpensive. In contrast with the common hair treating compositions, which often use strongly alkaline ingredients that are hard on the hair, the instant composition is effective in neutral and slightly acidic media, the potential for irritation, burns, or allergic reactions being minimized.

The invention should become readily apparent to a person having ordinary skill in the art, given the detailed disclosure thereof contained herein.

DETAILED DESCRIPTION OF THE PRESENT INVENTION

The composition and treatment of the instant invention employs Coulteria tinctoria pod extract, preferably after elevate temperature processing. The composition, most conveniently, is formulated and applied as a paste or cream, but may be formulated as a powder to which water is added.

In its simplest form, the liquid pod extract is used, from which a thixotropic paste is readily obtainable by adding an appropriate amount of starch.

The pod extract is prepared by soaking or percolating comminuted pods in water, at temperatures above approximately 100° C., preferentially above 150° C. The increased temperature of preparation enhances greatly the hair treating capacity of the extract.

An alternative is to treat the common pod extract, prepared at temperatures up to 100° C. and of small activity and then to temperatures above 100° C., preferably above 150° C., in order to obtain the highly active extract.

The extract can be refined, concentrated, crystallized, and/or spray-dried, before or after activation by high temperatures.

The following examples define with specificity the formulation of two compositions and corresponding treatments contemplated by this invention.

EXAMPLE 1 (CREAM OR PASTE)

100kg of Coulteria tinctoria pods were extracted countercurrently with 1000 kg of water, at 60°, until no solubles remained in the solids. The solution was evaporated to 5.0% by weight of solids and heated in an autoclave to 160° C. for 5 hours. To 10 kg of the resulting solution, 1.7 kg of corn starch were added, heated to 85°, until a smooth paste was obtained, which was packed in suitable containers. This procedure provided a ratio of about 5.88 parts of solution to one part corn starch. About 200 g of the paste was applied to curly, grayish hair and left for 30 minutes. After washing and drying, the hair was much softer, less curly, shiny and black.

EXAMPLE 2 (POWDER)

100 kg of Coulteria tinctoria pods were extracted with 200 kg of water in an autoclave at 170° for 5 hours. After cooling the solids were filtered off and the filtrate spray-dried. One kg of the dried extract was milled with 5 kg of soluble corn starch until a homogenous powder was obtained. Thirty-five grams of the powder and 200 ml of water were stirred until a smooth cream was obtained, which was applied to a straight, grayish, dull hair, of rather harsh texture. After 1 hour, the hair was washed and dried on medium-size bobs. The dried hair was soft, lustrous and black, with gentle permanent wave.

The treatments, two of which are identified above, fall within the generalized application steps which include thoroughly plastering the hair with the paste-like composition and covering the hair with a plastic cap for 30-60 minutes. The resident time is selected to achieve the desired degree of relaxation. Once the appropriate time has passed, the cap is removed and the hair washed with ordinary shampoo and cream rinse. The hair is then allowed to dry while subject to appropriate shaping means (curlers, bobs, wrapping, etc.). For example, if complete straightening is the objective, then the hair should be stretched around the head and pinned. Alternatively, if smooth undulating hair is desired then the hair should be rolled onto large hair bobs. As noted above, the composition dyes the hair, resulting in a deep lustrous black color. Also, repeated treatment maintains the selected shape and color while effectively reshaping any new growth without damaging the hair.

While described generally in the context of living hair, the treatment is equally effective for cut hair, preferably human, used for wigs and the like.

Given the foregoing, many variations and modifications of compositions and treatments should now be apparent to the skilled artisan. Accordingly, those variations and modifications are intended to fall within the spirit and scope of this invention as defined by the following claims.

I claim:

1. A composition for treating (conditioning, relaxing, reshaping) hair, comprising Coulteria tinctoria pod extract that has been previously activated by high temperature.

2. A composition according to claim 1, produced by heating the extract to a temperature in the range of 100° to 170° C.

3. A composition according to claim 1, produced by heating the extract to a temperature of substantially 160° C.

4. The method of producing a hair reshaping composition comprising the steps of
   heating a quantity of water containing approximately one-tenth the quantity by weight of Coulteria tinctoria to approximately 60° C.;
   maintaining the heating of water and pods until substantially no solubles remain in the solid material of the pods in the solution thus formed;
   evaporating the solution to approximately 5% by weight of solids to a temperature in the range of approximately 150° C. to at least 160° C. for 5 hours;
   producing a smooth paste by heating the solution at approximately 85° C. in the presence of a thickening agent.

5. The method according to claim 6, wherein the thickening agent is corn starch added in a ratio of solution to corn starch of approximately 5.88 to 1.

6. The method of producing a hair dyeing and reshaping composition comprising the steps of
   heating a quantity of water containing approximately one-half by weight of Coulteria tinctoria pods to a temperature of approximately 170° C. for 5 hours;
   removing residual solids;
   drying the residual liquid;
   melting the dried material with approximately five times as much of a soluble thickening agent, to produce a homogenous powder.

* * * * *